United States Patent
Chenchal et al.

(10) Patent No.: US 11,526,762 B2
(45) Date of Patent: Dec. 13, 2022

(54) METHOD AND SYSTEM OF TRAINING A MACHINE LEARNING NEURAL NETWORK SYSTEM FOR PATIENT MEDICAL STATES

(71) Applicant: Ventech Solutions, Inc., Columbus, OH (US)

(72) Inventors: Satish Chenchal, Ashburn, VA (US); Ravi Kunduru, Columbus, OH (US)

(73) Assignee: Ventech Solutions, Inc., Columbus, OH (US)

( * ) Notice: Subject to any disclaimer, the term of this patent is extended or adjusted under 35 U.S.C. 154(b) by 583 days.

(21) Appl. No.: 16/662,194

(22) Filed: Oct. 24, 2019

(65) Prior Publication Data
US 2021/0125072 A1   Apr. 29, 2021

(51) Int. Cl.
| | | |
|---|---|---|
| G06K 9/62 | (2022.01) | |
| G16H 50/20 | (2018.01) | |
| G06N 3/08 | (2006.01) | |
| G06N 3/04 | (2006.01) | |
| G16H 10/60 | (2018.01) | |

(52) U.S. Cl.
CPC ........... *G06N 3/084* (2013.01); *G06K 9/6264* (2013.01); *G06N 3/04* (2013.01); *G06N 3/082* (2013.01); *G16H 10/60* (2018.01); *G16H 50/20* (2018.01)

(58) Field of Classification Search
CPC combination set(s) only.
See application file for complete search history.

(56) References Cited

U.S. PATENT DOCUMENTS

| | | | |
|---|---|---|---|
| 8,023,710 B2 * | 9/2011 | Summers | A61B 5/7267 382/128 |
| 8,806,647 B1 | 8/2014 | Daswani | |
| 2013/0227695 A1 | 8/2013 | Shankar | |
| 2013/0232472 A1 | 9/2013 | Korner | |
| 2013/0290322 A1 | 10/2013 | Prosnitz | |
| 2020/0311535 A1 * | 10/2020 | Shrivastava | H03F 3/45179 |
| 2020/0401938 A1 * | 12/2020 | Etkin | G06V 10/768 |
| 2021/0034753 A1 * | 2/2021 | Canada | G06N 3/084 |
| 2021/0125072 A1 * | 4/2021 | Chenchal | G16H 50/70 |
| 2021/0264281 A1 * | 8/2021 | Pasupuleti | G06N 3/0454 |

OTHER PUBLICATIONS

Liang et al. (G. Liang, H. Hong, W. Xie and L. Zheng, "Combining Convolutional Neural Network With Recursive Neural Network for Blood Cell Image Classification," in IEEE Access, vol. 6, pp. 36188-36197, 2018, doi: 10.1109/ACCESS.2018.2846685.) (Year: 2018).*

* cited by examiner

*Primary Examiner* — Tahmina N Ansari
(74) *Attorney, Agent, or Firm* — Mahamedi IP Law LLP

(57) ABSTRACT

Method and system of training a machine learning neural network (MLNN). The method comprises receiving a set of input features at respective input layers of the MLNN. The MLNN implemented in a processor and comprises an output layer interconnected to input layers via intermediate layers. The input features are associated with input feature data of a patient medical condition. Then selecting, responsive to a data qualification threshold level, a subset of the input layers while deactivating a remainder of the set of input layers. The intermediate layers are configured with an initial matrix of weights. Then training the MLNN based at least in part upon adjusting the initial matrix of weights based on a supervised classification that provides, via the output layer, one of negative and positive patient diagnostic states.

18 Claims, 4 Drawing Sheets

300

Receiving a set of input features at respective ones of a set of input layers of a machine learning neural network (MLNN), the MLNN implemented in a processor and comprising an output layer interconnected to the set of input layers via a set of intermediate layers, each of the set of input features being associated with input feature data of a patient medical condition
310

Selecting, responsive to a data qualification threshold level being satisfied, a subset of the set of input layers while deactivating from the intermediate layers, a remainder of the set of input layers, the set of intermediate layers being configured in accordance with an initial matrix of weights
320

Training the MLNN In accordance with the subset of input layers based at least in part upon adjusting the initial matrix of weights in accordance with a supervised classification that provides, via the output layer, a patient diagnostic state output as one of a positive and a negative patient diagnostic states
330

> Receiving a set of input features at respective ones of a set of input layers of a machine learning neural network (MLNN), the MLNN implemented in a processor and comprising an output layer interconnected to the set of input layers via a set of intermediate layers, each of the set of input features being associated with input feature data of a patient medical condition
> 310
>
> ↓
>
> Selecting, responsive to a data qualification threshold level being satisfied, a subset of the set of input layers while deactivating, from the intermediate layers, a remainder of the set of input layers, the set of intermediate layers being configured in accordance with an initial matrix of weights
> 320
>
> ↓
>
> Training the MLNN In accordance with the subset of input layers based at least in part upon adjusting the initial matrix of weights in accordance with a supervised classification that provides, via the output layer, a patient diagnostic state output as one of a positive and a negative patient diagnostic states
> 330
>
> 300

↓

Deploying the MLNN as a trained MLNN upon producing a predetermined threshold percentage value of reduction in a number of false positive vulnerability defects associated with the initial matrix of weights
410

FIG. 4

METHOD AND SYSTEM OF TRAINING A MACHINE LEARNING NEURAL NETWORK SYSTEM FOR PATIENT MEDICAL STATES

TECHNICAL FIELD

The disclosure herein relates to neural network systems for data processing related to patient diagnostic states.

BACKGROUND

Healthcare diagnosis of patient medical states or conditions require medical information from myriad sources, ranging from global sources to local information from the community and from healthcare services and facilities, including patient-specific information from electronic records as well as based on interpersonal communications. Based on access to such comprehensive sources of medical information, healthcare systems are tasked with providing accurate and timely diagnoses and optimal outcomes for medical patients individually and also collectively.

Artificial intelligence (AI) and machine learning (ML) neural networks encode layered representation of input feature data, such as patient medical condition data, using input layers. The hierarchical feature representation of deep neural networks enable compact and precise encoding of input data. A deep learning architecture automatically learns the hierarchy of feature representations where progressively complex features are built on the top of the input features and other neural network layer data encodings.

BRIEF DESCRIPTION OF THE DRAWINGS

FIG. 3 illustrates a method of operation, in one example embodiment, of a system for neural network training of patient diagnostic states.

FIG. 4 illustrates a method of operation, in another example embodiment, of a system for neural network training of patient diagnostic states.

DETAILED DESCRIPTION

Figure 1:
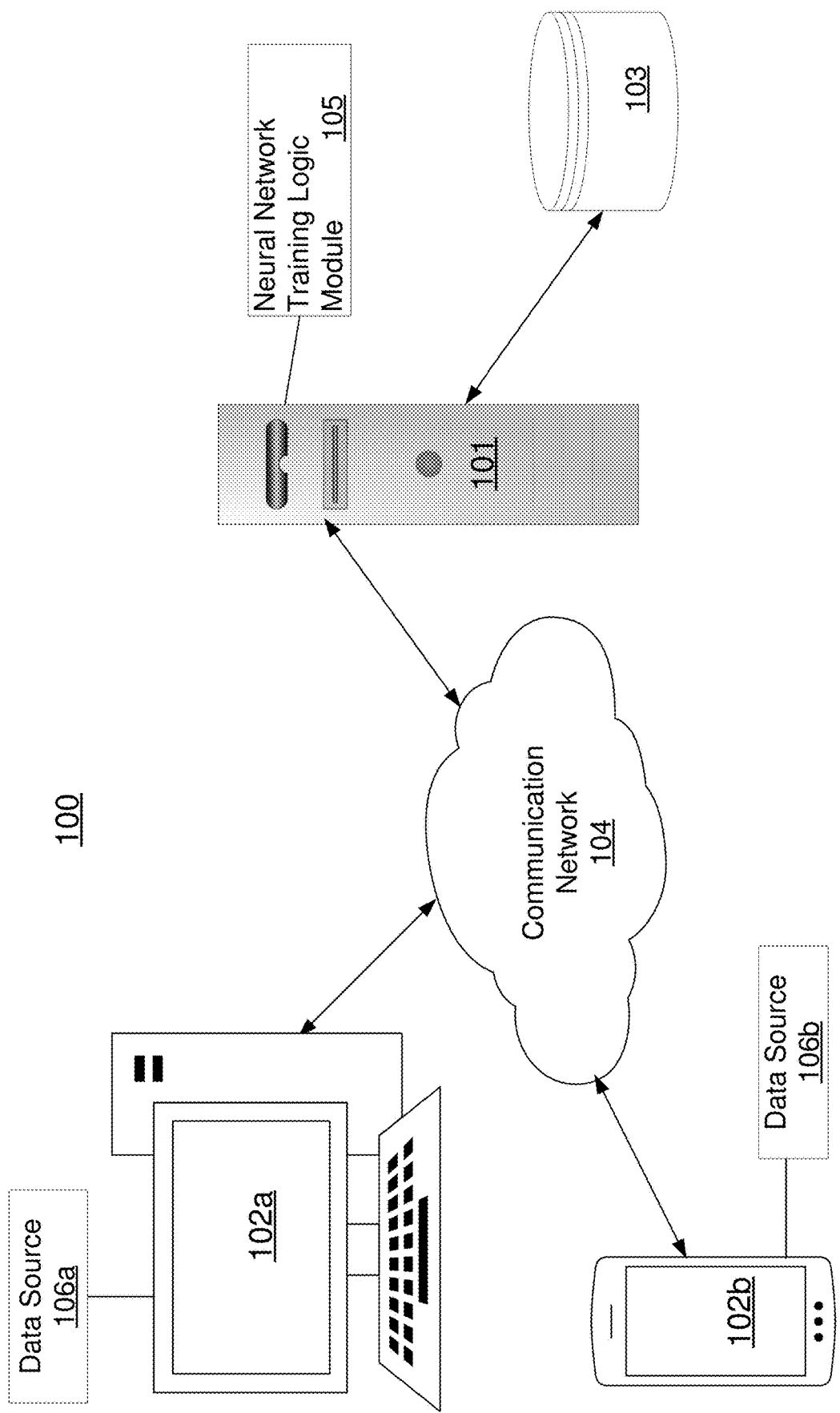
FIG. 1 illustrates, in an example embodiment, a cloud-based system for artificial intelligence (AI) based neural network training of patient diagnostic states.

Methods and systems provided herein, among other advantages, enable training of a machine learning neural network that accurately identifies patient diagnostic states or conditions by reducing the incidence of false positive diagnostic results for medical patients. In particular, solutions provided herein allow machine learning neural networks to be feasible for deployment and use even for large data sets as well as for complex images, as can be experienced in regard to machine learning applications for medical diagnosis and analysis. Among other benefits, solutions herein enable neural network training in accordance with dynamically selected input layers of the neural network, providing reduced computational power, increased computational efficiency, robust diagnostic accuracy and improved system response times associated with medical patient diagnosis and analysis.

The term "dynamic" as used herein refers to actions performed during real-time execution of the neural network training application.

As described herein, the neural networks, in embodiments, refer to an artificial intelligence (AI) based neural network, including machine learning (ML) or deep learning (DL) models. In a particular embodiment, the ML or neural network model herein may be implemented as a convolution neural network (CNN).

In accordance with a first example embodiment, provided is a method of training a machine learning neural network (MLNN). The method comprises receiving a set of input features at respective ones of a set of input layers of the MLNN, the MLNN implemented in a processor and comprising an output layer interconnected to the set of input layers via a set of intermediate layers, each of the set of input features being associated with input feature data of a patient medical condition; selecting, responsive to a data qualification threshold level being reached, a subset of the set of input layers while deactivating, from the intermediate layers, a remainder of the set of input layers, the set of intermediate layers being configured in accordance with an initial matrix of weights; and training the MLNN in accordance with the subset of input layers based at least in part upon adjusting the initial matrix of weights in accordance with a supervised classification that provides, via the output layer, a patient diagnostic state output as one of a positive and a negative patient diagnostic states.

In embodiments, training the neural network classifier comprises recursively adjusting the initial matrix of weights by backpropogation in diminishment of a number of the false positive patient diagnostic states generated at the output layer in accordance with the supervised classification.

In some embodiments, diminishment of the number of false positive patient diagnostic states proceeds, based on the recursively adjusting, in accordance with diminishment of an error matrix computed at the output layer of the neural network classifier.

In further aspects, the deploying proceeds once the trained classifier produces a predetermined threshold percentage value of reduction in a number of false positive patient diagnostic states associated with the initial matrix of weights.

In accordance with a second example embodiment, a non-transitory medium storing instructions executable in a processor of a server computing device is provided. The instructions, when executed in one or more processors, cause operations comprising receiving a set of input features at respective ones of a set of input layers of the MLNN, the MLNN implemented in a processor and comprising an output layer interconnected to the set of input layers via a set of intermediate layers, each of the set of input features being associated with input feature data of a patient medical condition; selecting, responsive to a data qualification threshold level being reached, a subset of the set of input layers while deactivating, from the intermediate layers, a remainder of the set of input layers, the set of intermediate layers being configured in accordance with an initial matrix of weights; and training the MLNN in accordance with the subset of input layers based at least in part upon adjusting the initial matrix of weights in accordance with a supervised classification that provides, via the output layer, a patient diagnostic state output as one of a positive and a negative patient diagnostic states.

In accordance with a third example embodiment, a server computing system is provided. The server computing system comprises one or more processors and a non-transitory memory storing instructions. The instructions, when executed in the one or more processors, cause operations comprising receiving a set of input features at respective ones of a set of input layers of the MLNN, the MLNN implemented in a processor and comprising an output layer interconnected to the set of input layers via a set of intermediate layers, each of the set of input features being associated with input feature data of a patient medical condition; selecting, responsive to a data qualification threshold level being reached, a subset of the set of input layers while deactivating, from the intermediate layers, a remainder of the set of input layers, the set of intermediate layers being configured in accordance with an initial matrix of weights; and training the MLNN in accordance with the subset of input layers based at least in part upon adjusting the initial matrix of weights in accordance with a supervised classification that provides, via the output layer, a patient diagnostic state output as one of a positive and a negative patient diagnostic states.

One or more embodiments described herein provide that methods, techniques, and actions performed by a computing device are performed programmatically, or as a computer-implemented method. Programmatically by way of software applications, as referred to herein, means through the use of code or computer-executable instructions. These instructions can be stored in one or more memory resources of the computing device.

Furthermore, one or more embodiments described herein may be implemented through the use of logic instructions that are executable by one or more processors of a computing device, including a server computing device. These instructions may be carried on a computer-readable medium. In particular, machines shown with embodiments herein include processor(s) and various forms of memory for storing data and instructions. Examples of computer-readable mediums and computer storage mediums include portable memory storage units, and flash memory. A server computing device as described herein utilizes processors, memory, and logic instructions stored on computer-readable medium. Embodiments described herein may be implemented in the form of computer processor-executable logic instructions or programs stored on computer memory mediums.

System Description

FIG. 1 illustrates, in an example embodiment, a cloud-based system for artificial intelligence (AI) based neural network training of patient diagnostic states. Server computing system or server device 101, also referred to herein as server 101, includes neural network training logic module 105 embodied according to computer processor-executable instructions stored within a non-transitory memory. Server 101 is in communication via communication network 104 with computing devices 102a, 102b, collectively referred to herein as computing device 102. Database 103, for example storing enterprise data accessible to medical data source software application 106a, 106b under execution, is communicatively accessible to server 101, and also to computing devices 102a, 102b.

Computing device 102a can be a mobile computing device. Computing device 102b can be or a desktop or laptop computing device in some embodiments, collectively hosting, storing or acquiring medical patient data via patient medical data source application 106b for execution thereon. Medical data source software applications 106a, 106b in another embodiment may be a web-based application program that executes on computing devices 102a, 102b. Mobile device 102b can be used by a patient for personal medical data acquisition, such as for example, cardiovascular pulse data, blood pressure readings captured via data source application 106b. Mobile device 102b can report acquired or accessed medical patent data to server 101 for use in conjunction with neural network training module 105. On the other hand, mobile device 102a can be used to access or acquire patient medical data under more institutionally sanctioned or monitored contexts, for instance, by medical professional staff at medical clinics and hospitals. In some embodiments, patent medical data from such different data acquisition sources 102a and 102b, may be accorded different levels or degree of trust weightings in any subsequent analysis and diagnosis of patient medical conditions. For example, in some embodiments, data sourced from computing device 102a under more controlled contexts can be regarded as more trustworthy and accordingly of higher quality than data acquired or sourced from computing device 102b under less controlled, more interpersonal contexts. Data acquired or sourced from certain ones of computing device 102 can therefore be accorded a higher trust weighting than others of computing device 102, with the higher trust weighting accorded acknowledging, in some embodiments, such data as being necessarily of higher quality and/or reliability in some embodiments.

Figure 2:
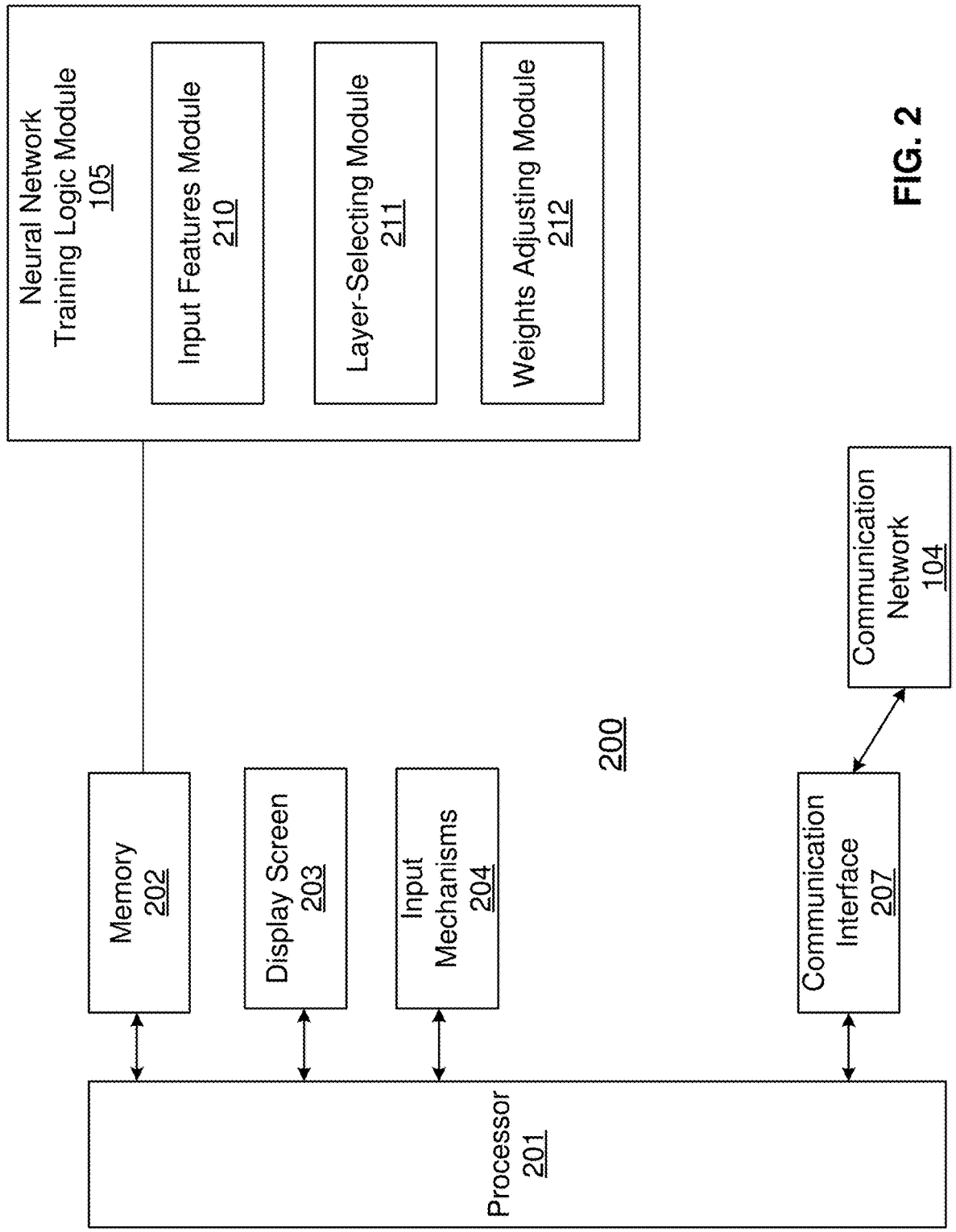
FIG. 2 illustrates, in one example embodiment, an architecture of a cloud-based server computing system for AI based neural network training of patient diagnostic states.

FIG. 2 illustrates, in one example embodiment, an architecture of a cloud-based server computing system for AI based neural network training of patient diagnostic states. Server computing system or device 101, also referred to herein as server 101, may include processor 201, memory 202, display screen 203, input mechanisms 204 such as a keyboard or software-implemented touchscreen input functionality, and communication interface 207 for communicating via communication network 104. Memory 202 may comprise any type of non-transitory system memory, storing instructions that are executable in processor 201, including such as a static random access memory (SRAM), dynamic random access memory (DRAM), synchronous DRAM (SDRAM), read-only memory (ROM), or any combination thereof.

Neural network training logic module 105 includes processor-executable instructions stored in memory 202 of server 101, the instructions being executable in processor 201. Neural network training logic module 105 may comprise portions or sub-modules including input features module 210, layer selecting module 211, and weights adjusting module 212.

Processor 201 uses executable instructions of input features module 210 receive a set of input features at respective ones of a set of input layers of the MLNN. In embodiments, the MLNN is implemented in a processor and comprises an output layer interconnected to the set of input layers via a set of intermediate layers, each of the set of input features being associated with input feature data of a patient medical condition.

In an embodiment, the input feature data includes at least one of image data, parametric measurement text data and a combination thereof.

In some variations, data sets of the input feature data are subject to data pre-processing, which can include image pre-processing, filtering and extraction of text data, or any combination thereof, as provided to the input layer of the neural network. The input feature data of a patient can be based on dietary, medical examination, laboratory testing results, and interpersonal interview or questionnaire, with multiple data files available under each group in some embodiments. The input feature data includes both image data and text data, related to patient conditions by way of bodily measurements, lipid measurements, medication intake and electro-cardio gram (ECG) readings in embodiments.

Processor 201 uses executable instructions stored in layer selecting module 211 to select, responsive to a data qualification threshold level being reached, a subset of the set of input layers while deactivating from the intermediate layers, a remainder of the set of input layers. In embodiments, the set of intermediate layers are configured in accordance with an initial matrix of weights.

In some aspects, the data qualification threshold relates to one or more of a data source category, a time proximity of data collection, a data density and a confidence level associated with the input feature data provided to the set of input layers.

The data density, in some embodiments, is an amalgamate of the number of images, the quality or resolution of the images, or a combination thereof. The data density, in an embodiment, is a measure of a quality and sufficiency of the input data for training the neural network to reliably and accurately perform patient medical diagnoses, once the neural network as trained is deployed.

In this manner, in accordance with the data source category, the time proximity of data collection, the data density and a confidence level associated with the input feature data provided to the set of input layers, only input layers having sufficient or high quality input data are selected for activation with one or more intermediate layers in creating the trained neural network. The remaining input layers having data density or other attributes below the data threshold are de-activated from neural network node computations, in part because the input data attributes below the threshold may not justify consumption of compute resources, including processor and memory resources.

In additional embodiments, as the input data attributes, such as data source category, the time proximity of data collection, the data density, rise to the level of a respective threshold requirement, the respective input layers which were previously de-activated can now be activated via being dynamically linked to establish active nodes of the intermediate layers for compute operations in the neural network, and are thus re-engaged in the neural network training. In embodiments, with regard to the time proximity of data collection, more recent data can be prioritized, or weighted more heavily, than older data. With regard to the data source category, data collected in more controlled or monitored contexts by medical professional staff may be weighted more heavily, or accorded a higher quality status, than more casually collected patient medical condition data.

Processor 201 uses executable instructions stored in weights adjusting module 212 to train the MLNN in accordance with the subset of input layers based at least in part upon adjusting the initial matrix of weights using a supervised classification that provides, via the output layer, a patient diagnostic state output as either a positive or a negative patient diagnostic medical condition or disease states.

In some aspects, training the neural network classifier comprises recursively adjusting the initial matrix of weights by backpropagation in diminishment of a number of the false positive patient diagnostic states generated at the output layer in accordance with the supervised classification. The adjusting, in some embodiments comprises recursively adjusting the initial matrix of weights by backpropagation in diminishment of a number of false positive patient diagnostic states rendered at the output layer.

In embodiments, diminishment of the number of false positive patient diagnostic states proceeds, based on the recursively adjusting, in accordance with diminishment of an error matrix computed at the output layer of the neural network classifier.

The supervised classification comprises identifying one of a positive and a negative patient diagnostic state to train the neural network. The term supervised classification as used herein refers to a supervised machine learning process which includes having a fully labeled set of data constituting known false positives while training the machine learning algorithm. Fully labeled means that each example in the training dataset is tagged with the finding of false positives that the algorithm, once trained as the matrix of weights is adjusted, should derive on its own.

The supervised classification, in some embodiments, is based at least on part on disease management analytic data associated with a plurality of patient diagnostic states.

The neural networks herein, in embodiments, refer to an artificial intelligence (AI) based neural network, including machine learning (ML) or deep learning (DL) models. In a particular embodiment, the ML or neural network model herein may be implemented as a convolution neural network (CNN).

To reduce incidences of false positive defect identifications, the training model may be implemented in accordance with executable instructions stored in weights adjusting module 212. The neural network, in one embodiment, is configured with a set of input layers, an output layer, and one or more intermediate layers connecting the input and output layers. In embodiments, the input layers are associated with input features that relate to medical parameter data of a patient, such as, but not limited to, patient data sourced or accessed via computing device 102.

In the particular embodiment of a convolution neural network model, the convolution operation typically embodies two parts of inputs: (i) input feature map data, and (ii) a weight (also referred to as output filter, or kernel). Given the input channel data with W(Width)×H(Height)×IC data cube and R×S×ICa filter, the output of direct convolution may be formulated as:

$$y_{w,h} = \sum_{r=0}^{R-1} \sum_{s=0}^{S-1} \sum_{c=0}^{C-1} x_{(w+r),(h+s),c} * w_{r,s,c}$$

where:
X=input data/input feature/input feature map
w=width of the input or output data
h=height of the input or output data
R=weight size (width)
S=weight size (height)
C=number of input channel
Y=output data/output feature/output feature map
W=filter/kernel/weight For each input channel, the filter, or weight, are convoluted with data and generates output data. The same location of data of all the input channels are summed together and generate 1 output data channel.

A weight is applied to detect a particular defect feature or type based on an input data stream of patient medical condition parameters.

Each output channel of the convolution model is represented by an output filter or weight used to detect one particular feature or pattern of the input feature data stream. Convolution networks may be constituted of many output filters or weights for each layer of the convolution model corresponding to respective features or patterns in the data stream of vulnerability defect types or features.

In some embodiments, the neural network is one of a recurrent neural network and a convolution neural network. In a convolution neural network, each neural network intermediate layer may correspond to a respective patient medical diagnostic state or result, in some embodiments. Examples of patient diagnostic states may include, for example, hypertension, a cardiovascular disease, diabetes among other medical diagnoses.

In embodiments, training the neural network classifier comprises recursively adjusting the initial matrix of weights by backpropogation in diminishment of a number of the false positive patient diagnostic states generated at the output layer in accordance with the supervised classification.

In some embodiments, the patient diagnostic state relates to a readmission prediction in accordance with a medical condition or a disease, such as for example, predicting a 30 day likelihood of patient readmission for a diabetes or a cardiovascular condition. In some variations, the input layer-selective machine learning techniques can used in neural network training to predict hypoglycemic event in a diabetic patient, based on parameters such as time and dosage of insulin, time and value of blood glucose measurement, diet, and physical activity of patients.

In some embodiments, the backpropagation comprises a backward propagation of errors in accordance with an error matrix as computed at the output layer, the errors being distributed backwards throughout the weights of the at least one neural network intermediate layer.

In some embodiments, diminishment of the number of false positive patient diagnostic states proceeds, based on the recursively adjusting, in accordance with diminishment of an error matrix computed at the output layer of the neural network classifier.

In some aspects, the MLNN is deployed as a trained MLNN upon producing a predetermined threshold percentage value of reduction in a number of false positive patient diagnostic states associated with the initial matrix of weights. The deploying proceeds once the trained classifier becomes capable of producing the predetermined threshold percentage value of reduction in a number of false positive patient diagnostic states associated with the initial matrix of weights. In an embodiment instance, the deploying proceeds once the trained classifier reaches at least an 90% reduction in the number false positive identifications associated with the initial matrix of weights of the intermediate layer of the neural network model.

Methodology

FIG. 3 illustrates a method of operation, in one example embodiment 300, of a system for neural network training of patient diagnostic states. Method 300 embodiment depicted is performed by one or more processors 201 of server computing device 101. In describing and performing the embodiments of FIG. 3, the examples of FIG. 1 and FIG. 2 are incorporated for purposes of illustrating suitable components or elements for performing a step or sub-step being described.

Examples of method steps described herein relate to the use of server 101 for implementing the techniques described. According to one embodiment, the techniques are performed by neural network training logic module 105 of server 101 in response to the processor 201 executing one or more sequences of software logic instructions that constitute neural network training logic module 105.

In embodiments, neural network training logic module 105 may include the one or more sequences of instructions within sub-modules including input features module 210, layer selecting module 211 and weights adjusting module 212. Such instructions may be read into memory 202 from machine-readable medium, such as memory storage devices. In executing the sequences of instructions contained in input features module 210, layer selecting module 211 and weights adjusting module 212 of neural network training logic module 105 in memory 202, processor 201 performs the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 310, processor 201 executes instructions of input features module 210 to receive a set of input features at respective ones of a set of input layers of the MLNN. In embodiments, the MLNN is implemented in a processor and comprises an output layer interconnected to the set of input layers via a set of intermediate layers, each of the set of input features being associated with input feature data of a patient medical condition.

In an embodiment, the input feature data includes at least one of image data, parametric measurement text data and a combination thereof.

In some variations, the data set is subject to data pre-processing, which can include image pre-processing, filtering and extraction of text data, or any combination thereof, as provided to the input layer of the neural network. In certain embodiments, the patient diagnostic states include a readmission prediction pertaining to a diagnostic state in accordance with a medical condition or a disease. The input feature data of a patient can be based on dietary, medical examination, laboratory testing results, and interpersonal interview or questionnaire regarding lifestyle features such as smoking, alcohol, and sleep patterns and history of hypertension and depression, a history of hospital facility admissions, with multiple data files available under each group in some embodiments.

At step 320, processor 201 of server computing device 101 executes instructions included in layer selecting module 211 to select, responsive to a data qualification threshold level being reached, a subset of the set of input layers while deactivating from the intermediate layers, a remainder of the set of input layers. In embodiments, the set of intermediate layers are configured in accordance with an initial matrix of weights.

In some aspects, the data qualification threshold relates to one or more of a data source category, a time proximity of data collection, a data density and a confidence level associated with the input feature data provided to the set of input layers.

The data density, in some embodiments, is an amalgamate of the number of images, the quality or resolution of the images, or a combination thereof. The data density, in an embodiment, is a measure of a quality and sufficiency of the input data for training the neural network to reliably and accurately perform patient medical diagnoses, once the neural network as trained is deployed.

In this manner, in accordance with the data source category, the time proximity of data collection, the data density and a confidence level associated with the input feature data provided to the set of input layers, only input layers having sufficient or high quality input data are selected for activation with one or more intermediate layers in creating the trained neural network. The remaining input layers having data density or other attributes below the data threshold are de-activated from neural network node computations, in part because the input data attributes below the threshold may not justify consumption of compute resources, including processor and memory resources.

In additional embodiments, as the input data attributes, such as data source category, the time proximity of data collection, the data density, rise to the level of a respective threshold requirement, the respective input layers which were previously de-activated can now be activated via being dynamically linked to establish active nodes of the intermediate layers for compute operations in the neural network, and are thus re-engaged in the neural network training. In embodiments, with regard to the time proximity of data collection, more recent data can be prioritized, or weighted more heavily, than older data. With regard to the data source category, data collected in more controlled or monitored contexts by medical professional staff may be weighted more heavily, or accorded a higher quality status, than more casually collected patient medical condition data.

At step 330, processor 201 executes instructions included in weights adjusting module 212 to train the MLNN in accordance with the subset of input layers based at least in part upon adjusting the initial matrix of weights using a supervised classification that provides, via the output layer, a patient diagnostic state output as either a positive or a negative patient diagnostic medical condition or disease states.

In some aspects, training the neural network classifier comprises recursively adjusting the initial matrix of weights by backpropogation in diminishment of a number of the false positive patient diagnostic states generated at the output layer in accordance with the supervised classification. The adjusting, in some embodiments comprises recursively adjusting the initial matrix of weights by backpropagation in diminishment of a number of false positive patient diagnostic states rendered at the output layer.

In embodiments, diminishment of the number of false positive patient diagnostic states proceeds, based on the recursively adjusting, in accordance with diminishment of an error matrix computed at the output layer of the neural network classifier. Classifiers applied are based on random forest, gradient boosting (GBM) and support vector (SVM) techniques in some embodiments.

The supervised classification comprises identifying one of a positive and a negative patient diagnostic state to train the neural network. The supervised classification, in some embodiments, is based at least on part on disease management analytic data associated with a plurality of patient diagnostic states. In certain embodiments, the patient diagnostic states include a readmission prediction pertaining to a diagnostic state in accordance with a medical condition or a disease, such as for example, predicting a 30 day likelihood of patient readmission for a diabetes or a cardiovascular condition. In some variations, the input layer-selective machine learning techniques can used in neural network training to predict hypoglycemic event in a diabetic patient, based on parameters such as time and dosage of insulin, time and value of blood glucose measurement, diet, and physical activity of patients.

In some aspects, the method comprises a first MLNN training iteration. The method further comprises at least a second MLNN training iteration that includes dynamically re-connecting at least one of the remainder input layers to the intermediate layers, responsive to a data density threshold being reached for the at least one of the remainder input layers.

The neural networks herein, in embodiments, refer to an artificial intelligence (AI) based neural network, including machine learning (ML) or deep learning (DL) models. In a particular embodiment, the ML or neural network model herein may be implemented as a convolution neural network (CNN).

FIG. 4 illustrates a method of operation 400, in another example embodiment, of a system for neural network training of patient diagnostic states. The method of operation 400 in the embodiment as depicted is performed in conjunction with method 300 as described in reference to FIG. 3.

At step 410, deploying the MLNN as a trained MLNN upon producing a predetermined threshold percentage value of reduction in a number of false positive patient diagnostic states associated with the initial matrix of weights. In some aspects, the deploying proceeds once the trained classifier becomes capable of producing the predetermined threshold percentage value of reduction in a number of false positive patient diagnostic states associated with the initial matrix of weights. In an embodiment instance, the deploying proceeds once the trained classifier reaches at least an 80% reduction in the number false positive identifications associated with the initial matrix of weights of the intermediate layer of the neural network model.

It is contemplated that embodiments described herein extend to individual elements and concepts described herein, as well as for embodiments to include combinations of elements recited anywhere in this application. Although embodiments are described in detail herein with reference to the accompanying drawings, it is to be understood that the invention is not limited to only such example embodiments. As such, many modifications and variations will be apparent to practitioners skilled in the art. Accordingly, it is intended that the scope of the invention be defined by the following claims and their equivalents. Furthermore, it is contemplated that a particular feature described either individually or as part of an embodiment can be combined with other individually described features, or parts of other embodiments, even if the other features and embodiments make no mention of the particular feature. Thus, the absence of describing combinations should not preclude the inventors from claiming rights to such combinations.

What is claimed is:

1. A method of training a machine learning neural network (MLNN), the method comprising:
receiving a set of input features at respective ones of a set of input layers of the MLNN, the MLNN implemented in a processor and comprising an output layer interconnected to the set of input layers via a set of intermediate layers, each of the set of input features being associated with input feature data of a patient medical condition;
selecting, responsive to a data qualification threshold level being reached, a subset of the set of input layers while deactivating from the intermediate layers, a remainder of the set of input layers, the set of intermediate layers being configured in accordance with an initial matrix of weights; and
training the MLNN in accordance with the subset of input layers based at least in part upon adjusting the initial matrix of weights in accordance with a supervised classification that provides, via the output layer, a patient diagnostic state output as one of a positive and a negative patient diagnostic states, wherein the adjusting comprises recursively adjusting the initial matrix of weights by backpropagation in diminishment of a number of false positive patient diagnostic states rendered at the output layer.

2. The method of claim 1 wherein diminishment of the number of false positive patient diagnostic states proceeds, based on the recursively adjusting, in accordance with diminishment of an error matrix computed at the output layer of the neural network.

3. The method of claim 1 wherein the input feature data includes at least one of image data, parametric measurement text data and a combination thereof.

4. The method of claim 3 further comprising deploying the MLNN as a trained MLNN upon producing a predetermined threshold percentage value of reduction in a number of false positive patient diagnostic states associated with the initial matrix of weights.

5. The method of claim 1 wherein the data qualification threshold relates to at least one of a data source category, a time proximity of data collection, a data density and a confidence level associated with the input feature data provided to the set of input layers.

6. The method of claim 1 wherein the supervised classification comprises identifying one of a positive and a negative patient diagnostic state.

7. The method of claim 6 wherein the supervised classification is based at least on part on disease management analytic data associated with a plurality of patient diagnostic states.

8. The method of claim 6 wherein the patient diagnostic states include a readmission prediction pertaining to one of a medical condition and a disease.

9. The method of claim 1 wherein the method comprises a first MLNN training iteration and further comprising at least a second MLNN training iteration that includes re-connecting at least one of the remainder input layers to the intermediate layers, responsive to a data density threshold being reached for the at least one of the remainder input layers.

10. A server computing system comprising:
a processor;
a non-transitory memory storing a set of instructions, the instructions when executed in the processor causing operations comprising:
receiving a set of input features at respective ones of a set of input layers of the MLNN, the MLNN implemented in a processor and comprising an output layer interconnected to the set of input layers via a set of intermediate layers, each of the set of input features being associated with input feature data of a patient medical condition;
selecting, responsive to a data qualification threshold level being reached, a subset of the set of input layers while deactivating from the intermediate layers, a remainder of the set of input layers, the set of intermediate layers being configured in accordance with an initial matrix of weights; and
training the MLNN in accordance with the subset of input layers based at least in part upon adjusting the initial matrix of weights in accordance with a supervised classification that provides, via the output layer, a patient diagnostic state output as one of a positive and a negative patient diagnostic states; wherein the adjusting comprises recursively adjusting the initial matrix of weights by backpropagation in diminishment of a number of false positive patient diagnostic states rendered at the output layer.

11. The server computing system of claim 10 wherein diminishment of the number of false positive patient diagnostic states proceeds, based on the recursively adjusting, in accordance with diminishment of an error matrix computed at the output layer of a neural network.

12. The server computing system of claim 10 wherein the input feature data includes at least one of image data, parametric measurement text data and a combination thereof.

13. The server computing system of claim 10, the instructions when executed in the processor causing operations further comprising deploying the MLNN as a trained MLNN upon producing a predetermined threshold percentage value of reduction in a number of false positive patient diagnostic states associated with the initial matrix of weights.

14. The server computing system of claim 10 wherein the data qualification threshold relates to at least one of a data source category, a time proximity of data collection, a data density and a confidence level associated with the input feature data provided to the set of input layers.

15. The server computing system of claim 10 wherein the supervised classification comprises identifying one of a positive and a negative patient diagnostic state.

16. The server computing system of claim 10 wherein the supervised classification is based at least on part on disease management analytic data associated with a plurality of patient diagnostic states.

17. The server computing system of claim 16 wherein at least one of the plurality of patient diagnostic states include a readmission prediction pertaining to one of a medical condition and a disease.

18. The server computing system of claim 10 wherein the instructions when executed in the processor causing operations further comprising a first MLNN training iteration and further comprising at least a second MLNN training iteration that includes re-connecting at least one of the remainder input layers to the intermediate layers, responsive to a data density threshold being reached for the at least one of the remainder input layers.

* * * * *